United States Patent
Redmond et al.

(10) Patent No.: US 6,699,262 B2
(45) Date of Patent: Mar. 2, 2004

(54) PERCUTANEOUS TISSUE TRACK CLOSURE ASSEMBLY AND METHOD

(75) Inventors: Russell J. Redmond, Goleta, CA (US); Claude A. Vidal, Santa Barbara, CA (US); Cary J. Reich, Los Gatos, CA (US); Felix Vega, San Francisco, CA (US)

(73) Assignee: Fusion Medical Technologies, Inc., Mountain View, CA (US)

( * ) Notice: Subject to any disclaimer, the term of this patent is extended or adjusted under 35 U.S.C. 154(b) by 143 days.

(21) Appl. No.: 09/957,176

(22) Filed: Sep. 19, 2001

(65) Prior Publication Data

US 2002/0026215 A1 Feb. 28, 2002

Related U.S. Application Data

(62) Division of application No. 09/361,663, filed on Jul. 27, 1999, now Pat. No. 6,334,865.
(60) Provisional application No. 60/095,306, filed on Aug. 4, 1998.

(51) Int. Cl.[7] ............................................. A61B 17/04
(52) U.S. Cl. ....................................... 606/213; 606/214
(58) Field of Search .................................. 606/213, 214

(56) References Cited

U.S. PATENT DOCUMENTS

| 4,744,364 A | 5/1988 | Kensey |
| 4,890,612 A | 1/1990 | Kensey |
| 5,108,421 A | 4/1992 | Fowler |
| 5,221,259 A | 6/1993 | Weldon et al. |
| 5,330,446 A | 7/1994 | Weldon et al. |
| 5,370,660 A | 12/1994 | Weinstein et al. |
| 5,383,896 A | 1/1995 | Gershony et al. |
| 5,413,571 A | 5/1995 | Katsaros et al. |
| 5,419,765 A | 5/1995 | Weldon et al. |
| 5,486,195 A | 1/1996 | Myers et al. |
| 5,591,205 A | 1/1997 | Fowler |
| 5,626,601 A | 5/1997 | Gershony et al. |
| 5,653,730 A | 8/1997 | Hammerslag |
| 5,728,132 A | 3/1998 | Van Tassel et al. |
| 5,752,974 A | 5/1998 | Rhee et al. |
| 5,855,559 A | 1/1999 | Van Tassel et al. |
| 6,045,570 A | 4/2000 | Epstein et al. |
| 6,193,670 B1 | 2/2001 | Van Tassel et al. |

FOREIGN PATENT DOCUMENTS

EP 0493810 EP 11/1995

Primary Examiner—Gary Jackson
(74) Attorney, Agent, or Firm—Townsend and Townsend and Crew, LLP

(57) ABSTRACT

A percutaneous tissue track closure assembly (2) includes a semipermeable barrier (26) mounted to the distal end of a tubular barrier carrier (20). The barrier is passed down a tissue track (12) and into a blood vessel (18) where the barrier is expanded to close off the blood vessel opening (14). A syringe device is used to drive a hemostatic flowable material (30) through a delivery tube (34) and into the tissue track. The semipermeable barrier permits blood to flow therethrough but prevents passage of the hemostatic flowable material therethrough. The hemostatic material includes a material which swells upon contact with blood, and a blood clotting agent. After an appropriate period of time, the barrier is collapsed and the barrier carrier and delivery tube are removed from the tissue track.

64 Claims, 10 Drawing Sheets

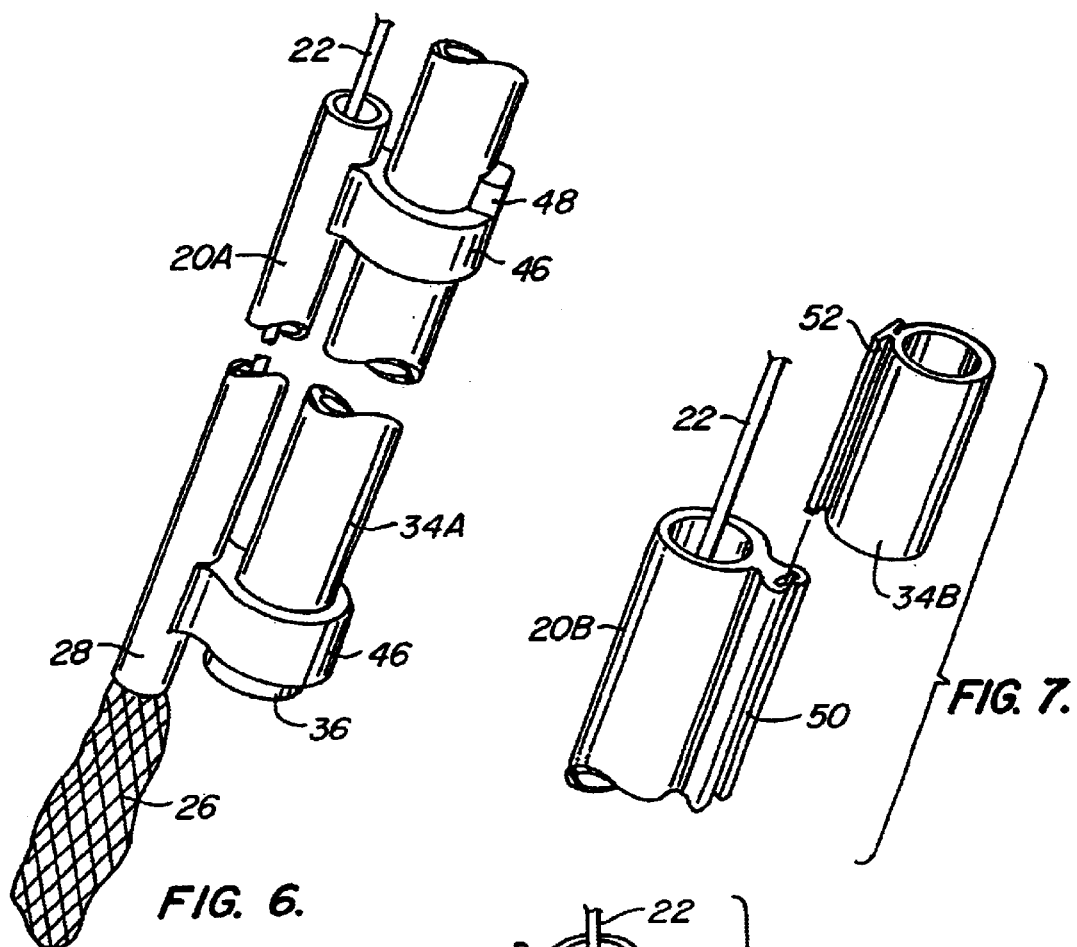
FIG. 6.
FIG. 7.
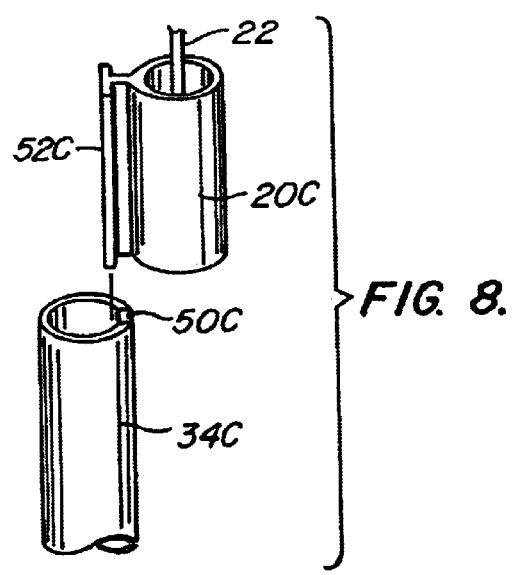
FIG. 8.

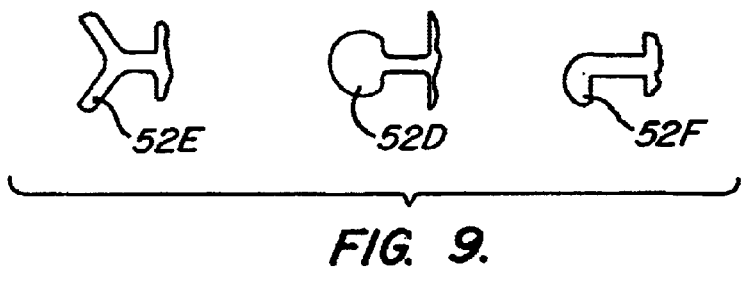
FIG. 9.
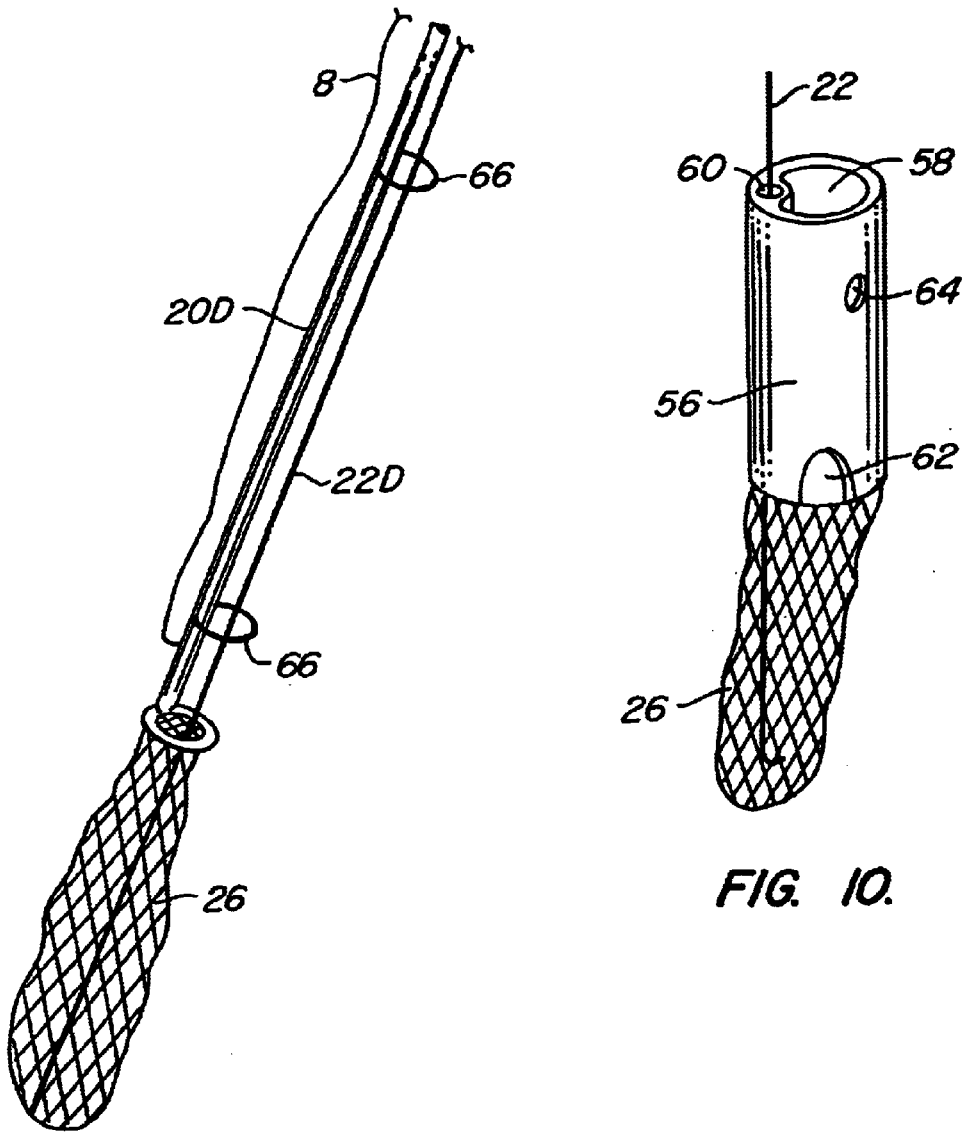
FIG. 10.
FIG. 11.

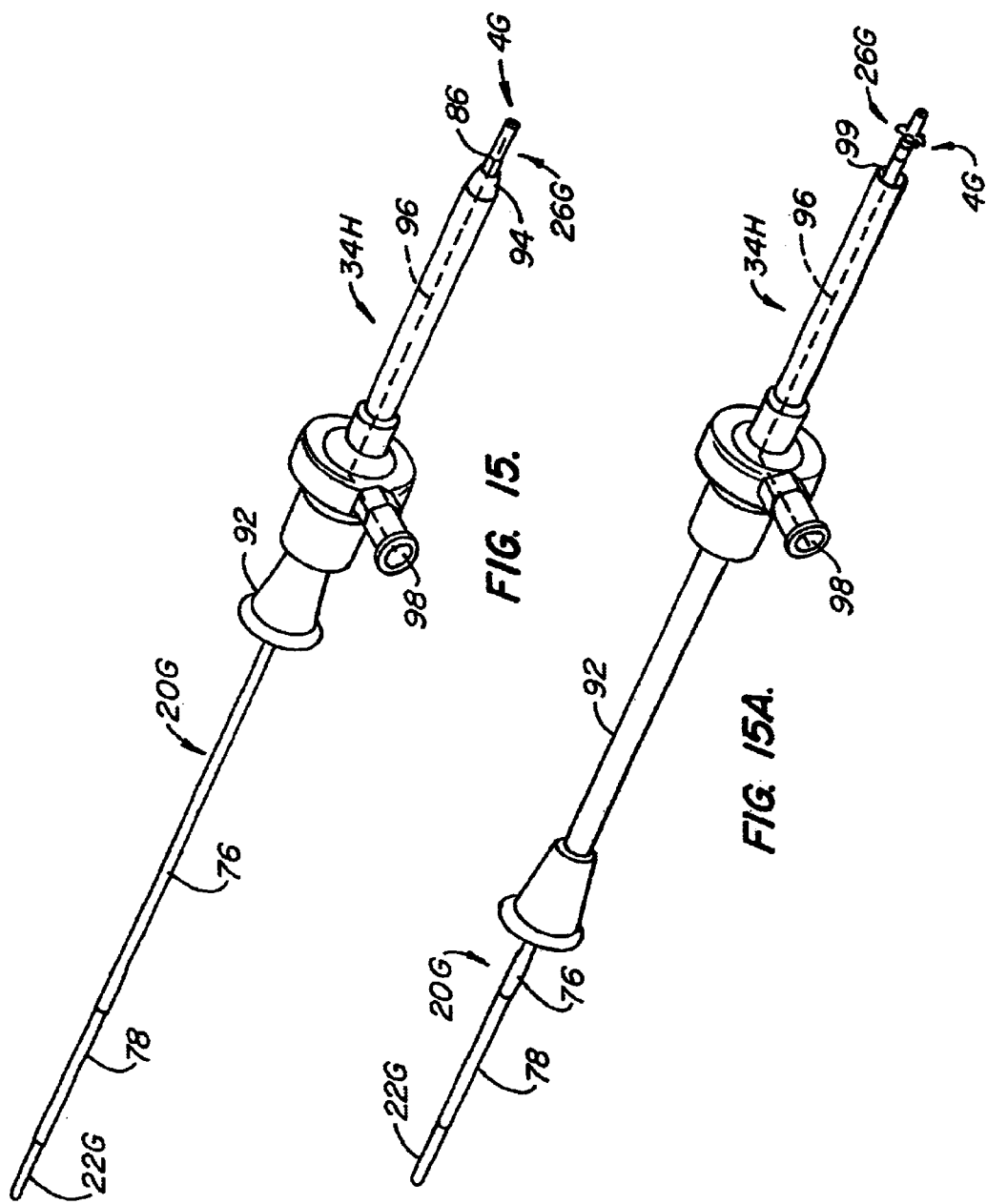

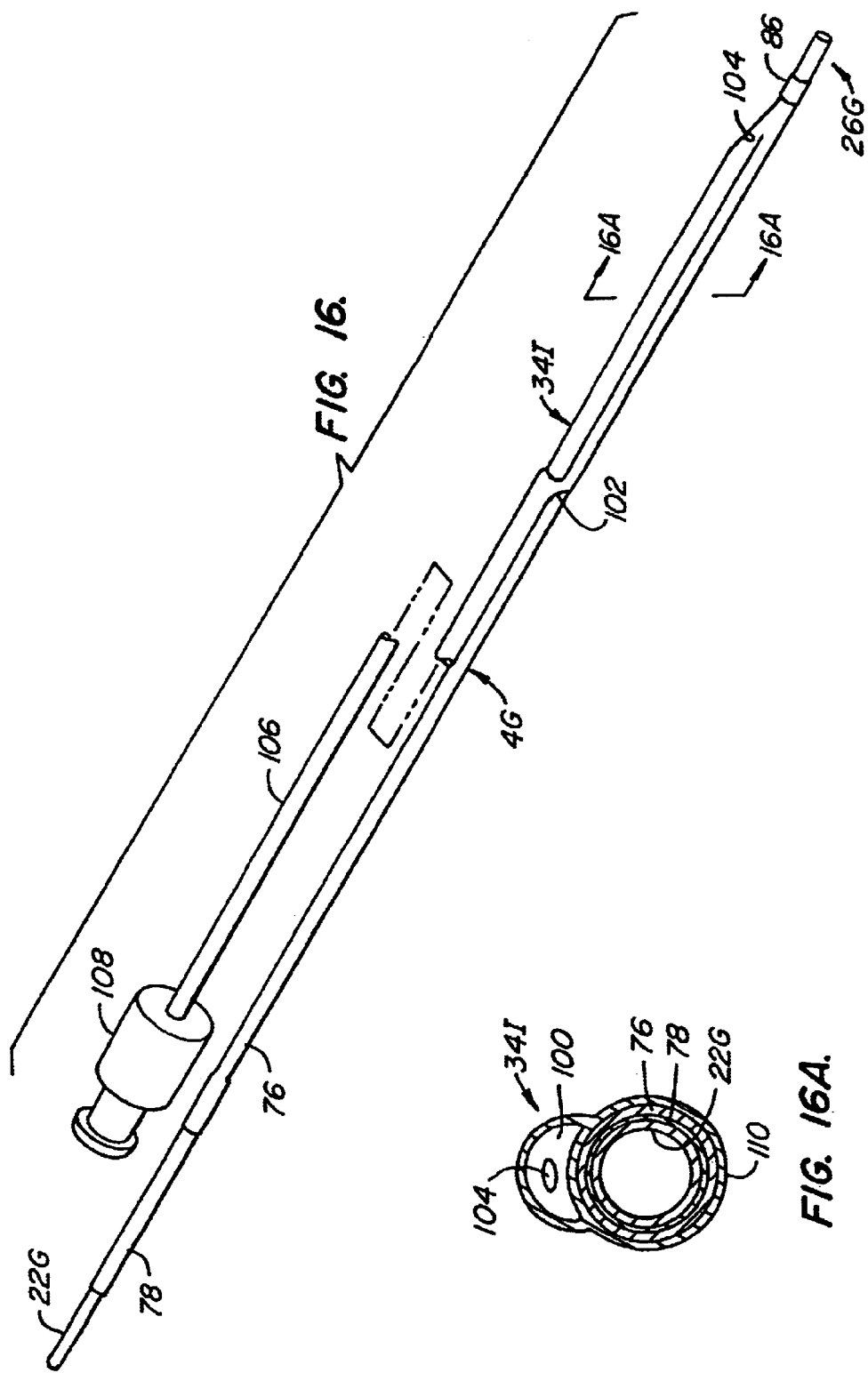

PERCUTANEOUS TISSUE TRACK CLOSURE ASSEMBLY AND METHOD

CROSS-REFERENCE TO RELATED APPLICATIONS

This application is a division of and claims the benefit of priority from application Ser. No. 09/361,663, filed on Jul. 27, 1999 now U.S. Pat. No. 6,334,865, which claimed the benefit of priority from Provisional Patent Application No. 60/095,306, filed Aug. 4, 1998, the full disclosures of which are incorporated herein by reference.

BACKGROUND OF THE INVENTION

Various therapeutic and diagnostic medical procedures involve accessing a vein or artery through a percutaneous tissue track. Femoral arteries are commonly accessed during various procedures, such as angiograms, angioplasties, catheterization and peripheral artery angioplasty. Accessing the blood vessel typically includes insertion of a relatively large diameter introducer sheath along the percutaneous tissue track and into an access opening in the blood vessel. Medical instruments, including guidewires and various catheters, are then introduced into the patient's vascular system through the introducer sheath.

At the conclusion of the medical procedure, the introducer sheath is removed leaving a relatively large access opening in the vessel wall which must be closed to stop bleeding. This has been traditionally accomplished through the use of digital pressure at the puncture site. This, however, requires that direct pressure be applied for an extended period of time, such as 45 minutes to an hour, to effectively stop bleeding from the access opening. Mechanical substitutes for finger pressure have been used, but can be uncomfortable for the patient. Using digital pressure to stop bleeding is not only expensive from the standpoint of the time of the trained medical person applying the pressure, it is also quite physically difficult to maintain a constant pressure at the puncture site for such an extended period. In addition, applying direct pressure to the puncture site causes the vessel being accessed to be blocked which can create its own problems, such as ischemia.

An early alternative to direct pressure to stop bleeding from an access opening in a blood vessel was the use of biodegradable collagen plugs. These plugs are either applied directly on top of the puncture site in the vessel wall, or are secured to the wall with a suture and polymer anchor. In the latter device, the polymer anchor is placed within the artery, against the inner wall of the artery. While such a device worked, it is not desirable to leave a foreign object within the blood vessel.

In lieu of applying direct pressure to the puncture site, hemostasis materials have been used to halt blood flow from the blood vessel access opening. These materials are typically positioned along the percutaneous tissue track using a balloon catheter, the balloon being situated at the distal end of the catheter within the blood vessel. When the balloon is inflated, it effectively seals the opening in the blood vessel to permit the hemostatic material to be properly positioned at the access opening in the blood vessel without being introduced into the vessel. After a period of time, the balloon is deflated and the balloon catheter is withdrawn from the blood vessel and tissue track. These devices require a very small balloon and can be expensive.

SUMMARY OF THE INVENTION

The present invention is directed to a percutaneous tissue track closure assembly and a method for sealing the percutaneous tissue track using a semipermeable barrier at the end of the tissue track and hemostatic flowable material within the tissue track so that blood or blood components passing through the semipermeable barrier interact with the hemostatic material to effectively seal the tissue track. The hemostatic material preferably includes both material which swells upon contact with blood or other aqueous fluids and material which causes blood to clot. Using the semipermeable barrier prevents passage of the hemostatic flowable material through the blood vessel access opening and into the blood vessel, while permitting a relatively controlled amount of blood to flow into the percutaneous tissue track to interact with the hemostatic flowable material. One aspect of the invention relates to a method for sealing the percutaneous tissue track. A semipermeable barrier is established at the distal end of the tissue track at the blood vessel puncture site. Hemostatic material is introduced into the tissue track. The semipermeable barrier permits blood, or at least one blood component, to pass from the blood vessel into the tissue track to interact with the hemostatic material and effectively seal the tissue track. The semipermeable barrier prevents the hemostatic material from passing through the access opening and into the blood vessel.

A percutaneous tissue track closure assembly includes broadly a barrier assembly, a flowable material assembly and a delivery tube alignment device. The barrier assembly includes an elongate barrier carrier, typically a tube, having a distal end. The barrier is mounted to the distal end of the barrier carrier. In a preferred embodiment the semipermeable barrier permits blood or blood components to pass through the barrier, but prevents the passage of the hemostatic flowable material through the barrier into the vessel. The barrier can be placed in a laterally retracted, undeployed configuration for passage into and out of the blood vessel, and in a laterally expanded, deployed configuration, when in the blood vessel, by a user-operated barrier actuator. The barrier actuator is, in one embodiment, in the form of a thin wire extending from the barrier and through the tubular barrier carrier; the barrier actuator is pushed to place the barrier in the undeployed configuration and pulled to expand the barrier into its laterally expanded, deployed configuration so the barrier can be used to block the access opening in the blood vessel. In another embodiment, the barrier actuator is in the form of two coaxial tubes, the outer one extending from the barrier and acting as barrier carrier, and the inner one bonded to the outer one at the distal end and acting as a barrier actuator. The outer tube is slit in several places, such as four, in the distal area located directly under the barrier. When the inner tube is pulled proximally relative to the outer tube, the sections of the outer tube located between the slits buckle outwardly and extend into arms which force the barrier to expand into a discus-like or mushroom shape.

In a further embodiment, a barrier carrier is in the form at least one barrier carrier tube, and preferably in the form of inner and outer barrier carrrier tubes, having longitudinally-extending weakened regions, the weakened regions typically being slits formed near the distal ends. The weakened regions of the inner barrier carrier tube are circumferentially offset from the weakened regions of the outer barrier carrier tube. A barrier actuator, typically in the form of a pull wire or tube, is used to pull on the distal ends of both inner and outer barrier carrier tubes causing the inner and outer barrier carrier tubes to buckle at the weakened regions thus causing the arms defined between the weakened regions to be deflected outwardly creating gaps therebetween. The laterally extending arms of the inner barrier carrier tube extend between the gaps created between the arms of the outer barrier carrier tube. The arms create fluid-flow-permitting gaps therebetween. It has been found by properly sizing these fluid-flow-permitting gaps, a semipermeable membrane need not be used. Depending upon the maximum size permitted for the fluid-flow-permitting gaps, it may be possible to eliminate the need for the inner barrier carrier tube. Also, in some cases a third barrier carrier tube with its own set of laterally-expandable arms may be used.

The flowable material assembly includes a delivery tube and a source of a hemostatic flowable material, typically a syringe device. The syringe device is mounted to the proximal end of the delivery tube. The delivery tube is positioned along the barrier carrier so that the distal end of the delivery tube is adjacent the distal end of the barrier carrier through the use of the delivery tube alignment device.

The elongate barrier carrier may be mounted within the delivery tube to define a flowable material path between the two. The flowable material path may be generally annular in shape.

The delivery tube may be in the form of a laterally collapsible tube. The laterally collapsible tube may be mounted to and be external of the elongate barrier carrier. This would permit the inside diameter of the introducer sheath, through which the barrier carrier and collapsible delivery tube is passed, to be of a smaller diameter than would be required if the delivery tube were not collapsible.

The distal ends of the barrier assembly and the delivery tube are inserted through the percutaneous tissue track so that the distal end of the barrier carrier extends through the access opening in the blood vessel so that the barrier is positioned within the blood vessel. Once within the blood vessel, the barrier actuator is operated to place the semipermeable barrier into the laterally expanded, deployed configuration so that the barrier can be positioned against and effectively cover the access opening in the blood vessel. The hemostatic flowable material is then directed into the percutaneous tissue track. As mentioned above, the semipermeable barrier is designed to prevent the hemostatic flowable material from entering the blood vessel. The hemostatic flowable material preferably includes a flowable gel material which swells upon contact with blood or other aqueous fluid, and a blood clotting agent which causes blood or blood components to clot, thus sealing the tissue track by creating an effective plug within the tissue track. After an appropriate period of time, which allows the blood to clot and the hemostatic flowable material to swell thus creating an effective plug in the tissue track, the barrier is placed into its laterally retracted, undeployed configuration and the barrier carrier and delivery tube are removed from the percutaneous tissue track; doing so permits the hemostatic flowable material to completely close the tissue track.

In one embodiment, the delivery tube alignment device includes a thread or other filament secured to the distal end of the barrier carrier. The thread or filament passes through the delivery tube and prevents the distal end of the delivery tube from moving distally past a chosen position along the barrier carrier. After being aligned, the proximal ends of the delivery tube and barrier carrier can be temporarily secured together using, for example, tape. The delivery tube alignment device may also comprise guides, secured to and extending laterally from one of the barrier carrier and delivery tube, which engage and slide along the other of the barrier carrier and delivery tube together, and a stop element that prevents movement of the distal end of the delivery tube past a chosen position at the distal end of the barrier carrier.

Another delivery tube alignment device includes indicia or marks on the delivery tube and the barrier carrier. While using marks or indicia to properly position the distal end of the delivery tube is quite simple from a manufacturing standpoint, it relies on visual alignment of the indicia rather than mechanical alignment of the parts.

Other features and advantages will appear from the following description in which the preferred embodiments have been set forth in detail in conjunction with the accompanying drawings.

BRIEF DESCRIPTION OF THE DRAWINGS

FIG. 6 illustrates an alternative embodiment of the invention in which the thread-type delivery tube alignment device of FIGS. 1–5 has been replaced by guides positioned along the barrier carrier which engage the delivery tube, the delivery tube including a stop to properly position the open distal end of the delivery tube relative to the distal end of the barrier carrier;

FIGS. 7 and 8 illustrate further alternative embodiments of the invention in which the barrier sheath and delivery tube include slides and slide openings to guide the delivery tube along the barrier sheath;

FIG. 9 illustrates three alternative embodiments of differently shaped slides which could be used with the embodiments of FIGS. 7 and 8;

FIG. 10 illustrates a further embodiment of the invention in which the barrier carrier and delivery tube are combined into a single structure including a main lumen, through which the flowable material passes, and a supplemental lumen, through which the barrier actuator passes, the combination tube having a number of flowable material exits at the distal end of the combination tube and along the length of the combination tube;

FIG. 11 illustrates an alternative embodiment of the barrier assembly of FIG. 2 in which the barrier sheath has been replaced by a solid barrier carrier with the barrier actuator being external of the barrier carrier and guided along the barrier carrier by several guide loops;

FIG. 15 illustrates the barrier assembly of FIG. 14 with a further embodiment of a delivery tube mounted over the barrier carrier of the barrier assembly;

FIG. 15A illustrates the device of FIG. 15 with the spacer tube retracted opening up an annular flowable material path between the delivery tube and the barrier sheath;

FIG. 16 illustrates a further embodiment of the invention in which the barrier assembly of FIG. 14 has a laterally-collapsible flowable material delivery tube mounted to it; and FIG. 16A is a cross-sectional view taken along line 16A—16A of FIG. 16 with the delivery tube in an expanded condition.

DESCRIPTION OF THE SPECIFIC EMBODIMENTS

Figure 4:
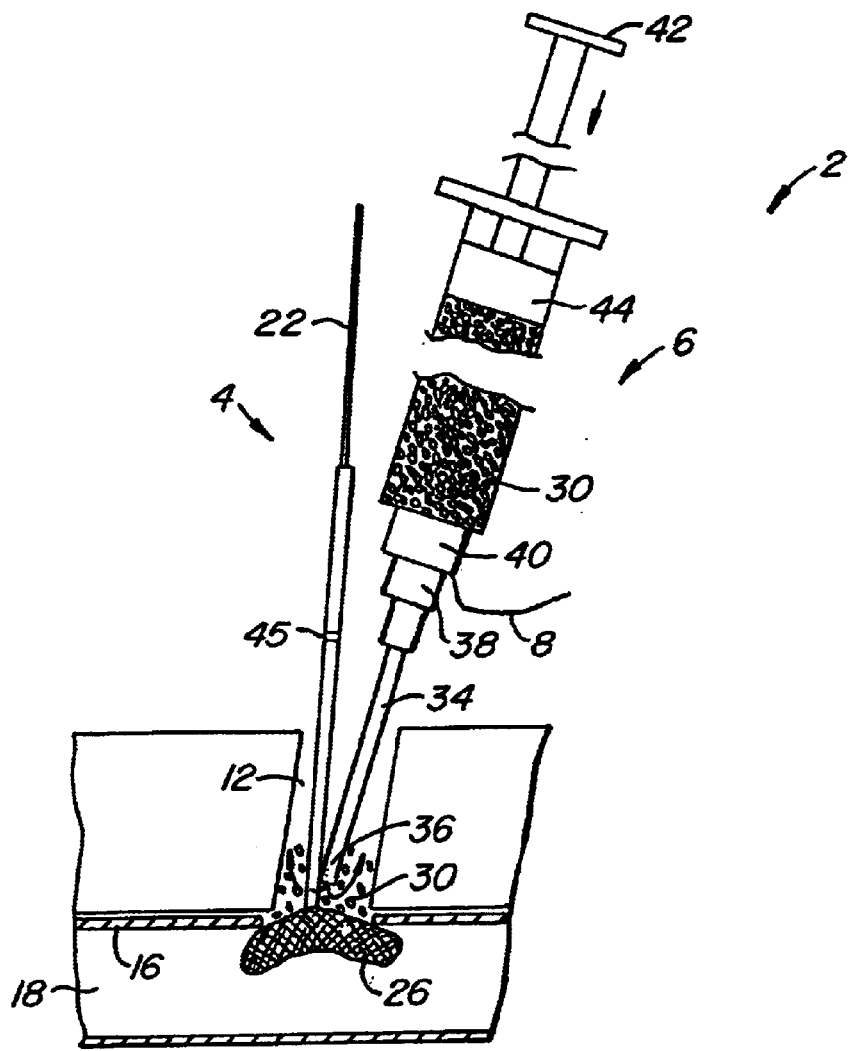
FIG. 4 illustrates a percutaneous tissue track closure assembly made according to the invention showing the barrier actuator extending from the open proximal end of the barrier sheath, a syringe filled with a hemostatic flowable material secured to the Luer fitting at the proximal end of the delivery tube and the introduction of the hemostatic flowable material from the syringe through the open distal end of the delivery tube into the percutaneous tissue track with the hemostatic flowable material being prevented from entering the blood vessel by the deployed barrier.

Referring initially to FIG. 4, a percutaneous tissue track closure assembly 2 is seen to include a barrier assembly 4, a thread 8 and a flowable material assembly 6 coupled to and aligned with the barrier assembly 4 using thread 8. Thread 8 acts as an alignment device for properly positioning the barrier assembly and flowable material assembly relative to one another as will be described in more detail below.

Figure 1:
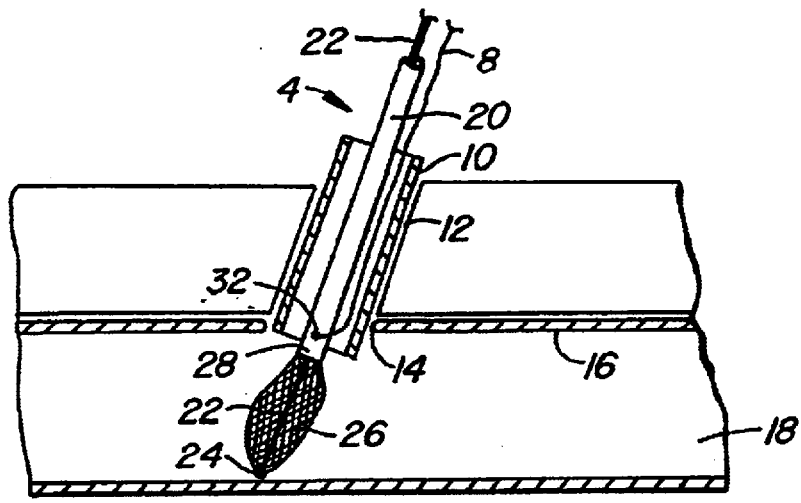
FIG. 1 illustrates an introducer catheter within a percutaneous tissue track and a barrier assembly passing through the introducer catheter with the semipermeable barrier within the blood vessel in its laterally retracted, undeployed configuration.

Referring now to FIG. 1, an introducer sheath 10 is shown extending along a percutaneous tissue track 12 and extending a short distance through an access opening 14 formed in the wall 16 of a blood vessel 18. Introducer sheath 10 had been used to introduce appropriate medical devices, such as guidewires and catheters, into blood vessel 18 during a prior therapeutic or diagnostic procedure. Before removing introducer sheath 10, the distal end of the barrier assembly 4 is passed through the introducer sheath.

Barrier assembly 4 includes a tubular barrier carrier 20 housing a flexible, wire-like barrier actuator 22 therein. The distal end 24 of barrier actuator 22 is secured to the center of a semipermeable barrier 26, the semipermeable barrier being connected to the distal end 28 of barrier carrier 20. Barrier 26 is constructed so that it can assume the laterally retracted, undeployed configuration of FIG. 1 or the laterally expanded, deployed configuration of FIG. 2 by either pushing or pulling on barrier actuator 22. Therefore, barrier actuator 22 is flexible but has sufficient columnar strength to move barrier 26 between the laterally expanded configuration of FIG. 2 and the laterally retracted configuration of FIG. 1. Barrier 26 is preferably a mesh-like material which permits a restricted flow of blood through the barrier but prevents a hemostatic flowable material 30, originally within syringe 6, from passing through barrier 26 and into blood vessel 18.

Figure 2:
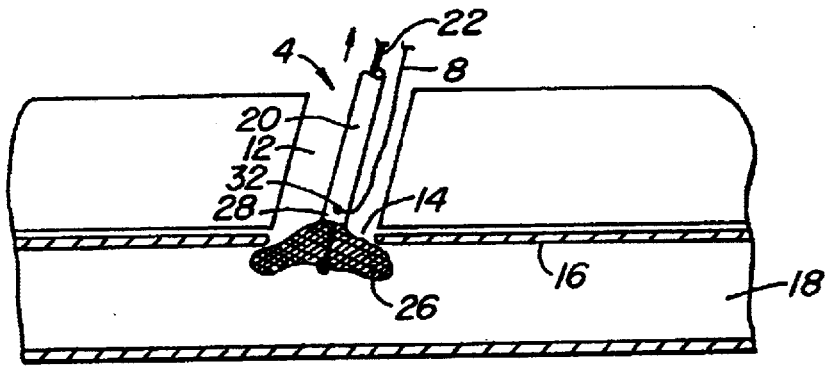
FIG. 2 is similar to FIG. 1, but with the introducer sheath removed from the percutaneous tissue track and the barrier in its laterally expanded, deployed configuration covering the access opening in the blood vessel.
Figure 3:
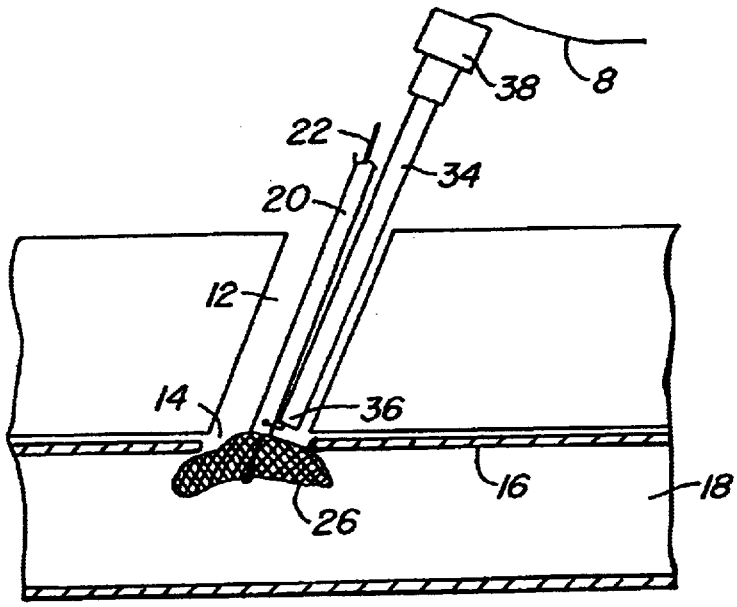
FIG. 3 shows a flowable material delivery tube passing over a thread extending from the distal end of the barrier sheath of FIG. 2, the distal end of the delivery tube being generally aligned with the attachment point of the thread to the barrier sheath.

FIG. 2 illustrates barrier assembly 4 within percutaneous tissue track 12 after barrier actuator 22 has been pulled to cause barrier 26 to be deformed into its laterally expanded, mushroom-like deployed configuration and introducer sheath 10 has been removed. FIG. 2 also illustrates thread 8 extending from a position 32 adjacent the distal end 28 of barrier carrier 20. FIG. 3 illustrates the placement of a flowable material delivery tube 34 over thread 8 until the open distal end 36 of tube 34, which acts as the delivery tube exit, is adjacent position 32 at the end of thread 8. As seen in FIG. 3, thread 8 extends out from the Luer fitting 38 at the proximal end of delivery tube 34. Luer fitting 38 is mounted to a Luer fitting 40 at the distal end of syringe 6. As shown in FIG. 4, thread 8 is captured between the Luer fittings 38, 40, thus securing open distal end 36 of delivery tube 34 adjacent position 32 along barrier carrier 20. At this point, the user depresses the thumb pad 42 of syringe 6 causing piston 44 to move distally in the direction of the arrow to force hemostatic flowable material 30 from syringe 6, through tube 34, out open distal end 36, and into tissue track 12.

FIG. 4 also shows alignment markings, indicators or indicia 45 on barrier carrier 20. Markings 45 can be used instead of or in addition to thread 8 as an alignment device. In FIG. 4, markings 45 are positioned to be aligned with the lower edge of Luer fitting 38 when distal end 36 is properly positioned.

Hemostatic flowable material 30 may be a material which either swells upon contact with an aqueous liquid, such as blood or aqueous blood components, or causes blood or one or more blood components to clot upon contact with the hemostatic flowable material, and preferably both. In the preferred embodiment, hemostatic flowable material 30 includes a bioabsorbable, flowable, granular gel as described in U.S. patent application Ser. No. 09/032,370, filed Feb. 27, 1998; Ser. No. 08/903,674, filed Jul. 31, 1997; Ser. No. 60/050,437, filed Jun. 18, 1997; and Ser. No. 08/704,852, filed Aug. 27, 1996, entitled Fragmented Polymeric Compositions and Methods for Their Use. In addition, hemostatic flowable material 30 includes thrombin or thrombin and fibrinogen as the clotting agent. Flowable material delivery tube 34 is preferably at least a 16 gauge, and preferably a 15 gauge, tube. Flowable material 30 can also include other agents, such as antibacterial agents, antifibrinolytic agents, or bacteriostatic agents.

In many applications, percutaneous tissue track 12 can be sufficiently filled without moving open distal end 36 of delivery tube 34 from the position as shown in FIG. 4. However, in some cases it may be desired to permit open distal end to be moved back out through tissue track 12 as material 30 is injected into the tissue track. Because thread 8 locks distal end 36 adjacent to position 32, this can be achieved only by either moving barrier assembly 4, which may not be desired until reactions have occurred with hemostatic flowable material 30 to create an effective plug, or by severing thread 8. One way to sever thread 8 would be to include a cutout or notch at distal end 36 of tube 34 so that the user could catch the end of thread 8 within the cutout or notch and then rotate assembly 6 until the thread is severed. At this point, open distal end 36 can be backed out of path 12 while maintaining barrier assembly 4 in place, thus back-filling tissue track 12.

Figure 5:
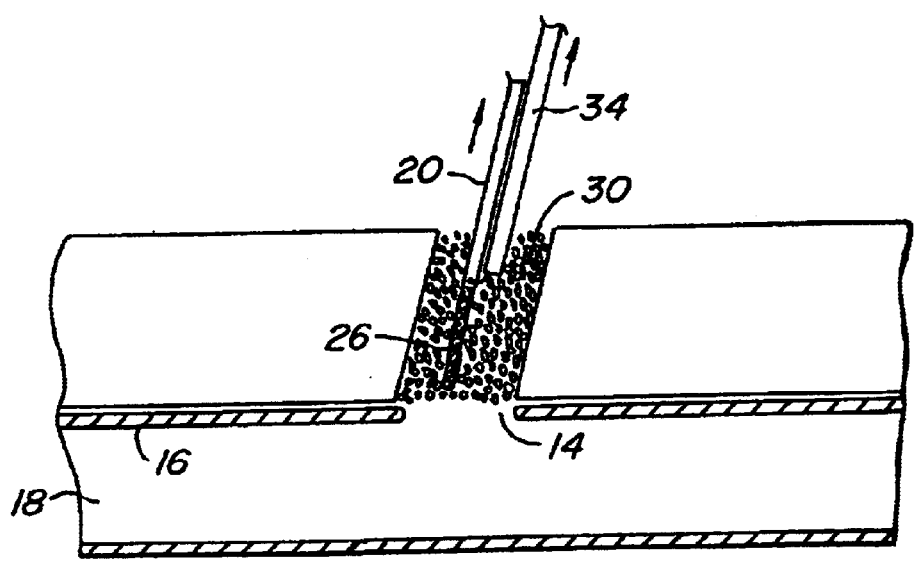
FIG. 5 illustrates the barrier assembly and delivery tube being withdrawn from the percutaneous tissue track after the percutaneous tissue track has been substantially filled with the hemostatic flowable material and the hemostatic flowable material has interacted with blood passing through the semipermeable barrier to effectively form a plug made of swollen flowable material and clotted blood.

After hemostatic flowable material has reacted sufficiently with blood or one or more blood components to form an effective plug within tissue track 12, barrier actuator 22 is extended to move barrier 26 from the deployed configuration of FIG. 2 to the undeployed configuration of FIG. 1; barrier assembly 4 can then be withdrawn from tissue track 12 as suggested in FIG. 5. Any opening or gap which may be left by the retreating barrier carrier 20 and tube 34 will be quickly filled by hemostatic flowable material 30.

While the use of thread 8 as a delivery tube alignment device is simple and inexpensive, it may be desired to use different structure for accomplishing this. FIGS. 6–10 illustrate alternative embodiments with like reference numerals referring to like elements.

Barrier carrier 20A, see FIG. 6, includes at least two delivery guides 46 which guide the movement of delivery tube 34A along barrier carrier 20A. Delivery tube 34A includes a stop 48 which engages the proximal-most guide 46 when the open distal end 36 of delivery tube 34A is properly aligned at the distal end 28 of barrier carrier 20A.

FIG. 7 illustrates a different type of guide element in which barrier carrier 20B includes a slide opening 50 and delivery tube 34B includes a complementary, T-shaped slide 52. Delivery tube 34B would preferably include a stop element similar to stop 48 of FIG. 6; such a stop element is not shown in FIG. 7. FIG. 8 illustrates an alternative embodiment of the structure of FIG. 7 in which slide opening 50C is formed in delivery tube 34C, rather than as a part of barrier carrier 20B, and slide 52C is formed as an extension of barrier carrier 20C. The fit between slide opening 50C and slide 52C may be relatively tight so that substantially no hemostatic flowable material can flow through the gap between the two. Alternatively, a portion of the length of engagement of slide opening 50C and slide 52C can be made to be a somewhat loose fit to permit hemostatic flowable material 30 to pass between the two in addition to flowing out of the open distal end of delivery tube 34C. Backing out, back-filling movements of the delivery tube are facilitated through the embodiments of FIGS. 6, 7 and 8. FIG. 9 illustrates three alternatively-shaped slides 52D, 52E and 52F which could be used with embodiments similar to the embodiments of FIGS. 7 and 8.

FIG. 10 illustrates an embodiment in which the barrier carrier and delivery tube are incorporated into a combination tube 56. Combination tube 56 includes a main lumen 58, through which flowable material 30 passes, and a supplemental lumen 60, through which barrier actuator 22 passes. Instead of having a single flowable material exit at the open distal end of combination tube 56, tube 56 has a number of flowable material exits 62, 64 along at least part of its length; this helps eliminate the need for backing the delivery tube out of tissue track 12 to back fill the tissue track with flowable material 30. Also, combination tube 56 acts as the barrier carrier alignment device to eliminate the need for thread 8 of FIGS. 1–5 and 11, markings 45 of FIG. 4, guides 46 and stop 48 of FIG. 6, and slide opening 50 and slides 52 of FIGS. 7–9.

FIG. 11 illustrates an embodiment in which the barrier carrier has been replaced by an elongate barrier carrier 20D. Barrier carrier 20D is solid but has a number of guide loops 66 extending from the barrier carrier along its length to guide barrier actuator 22.

Figure 12:
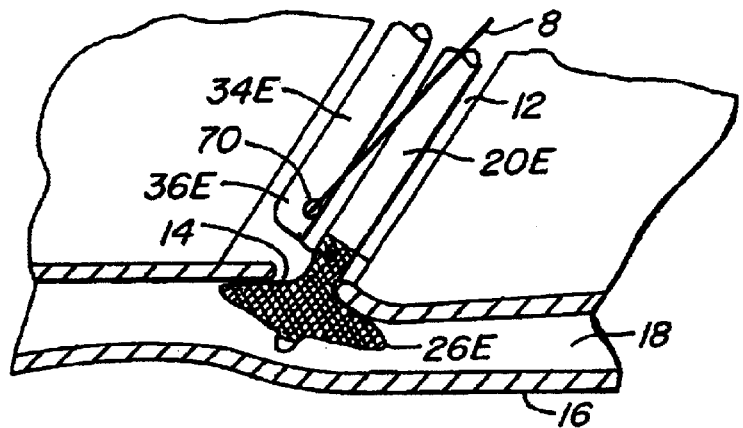
FIG. 12 is a view similar to FIG. 3 but with the thread passing out through a hole at the distal end of the flowable material delivery tube.

FIG. 12 illustrates a further embodiment in which thread 8 passes through the open distal end 36E of tube 34E and then through a hole 70 formed in tube 34E. This eliminates the need to sever thread 8 when it is desired to back-fill tissue track 12.

Figure 13:
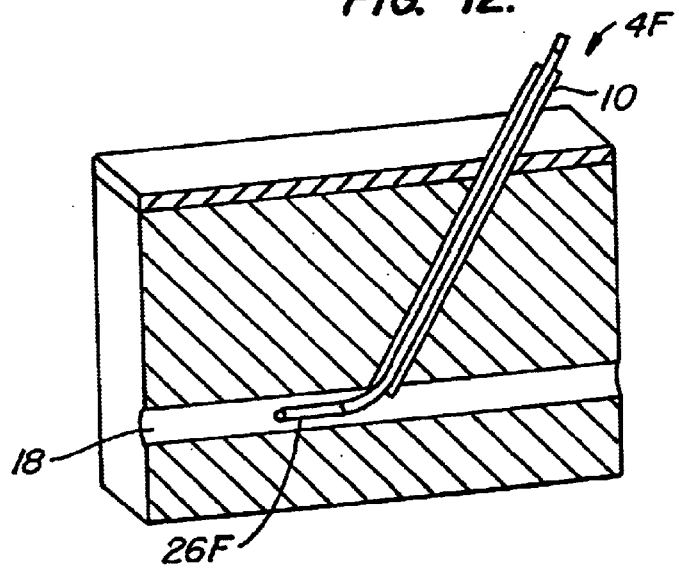
FIG. 13 illustrates an alternative embodiment of the barrier assembly of FIGS. 1–5 with the barrier within a blood vessel in a collapsed condition.
Figure 13A:
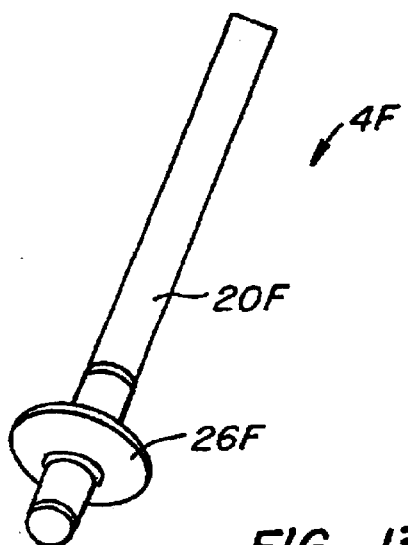
FIGS. 13A and 13B are enlarged views which show the distal end of the barrier assembly of FIG. 13 in a radially-expanded, deployed condition.
Figure 13B:
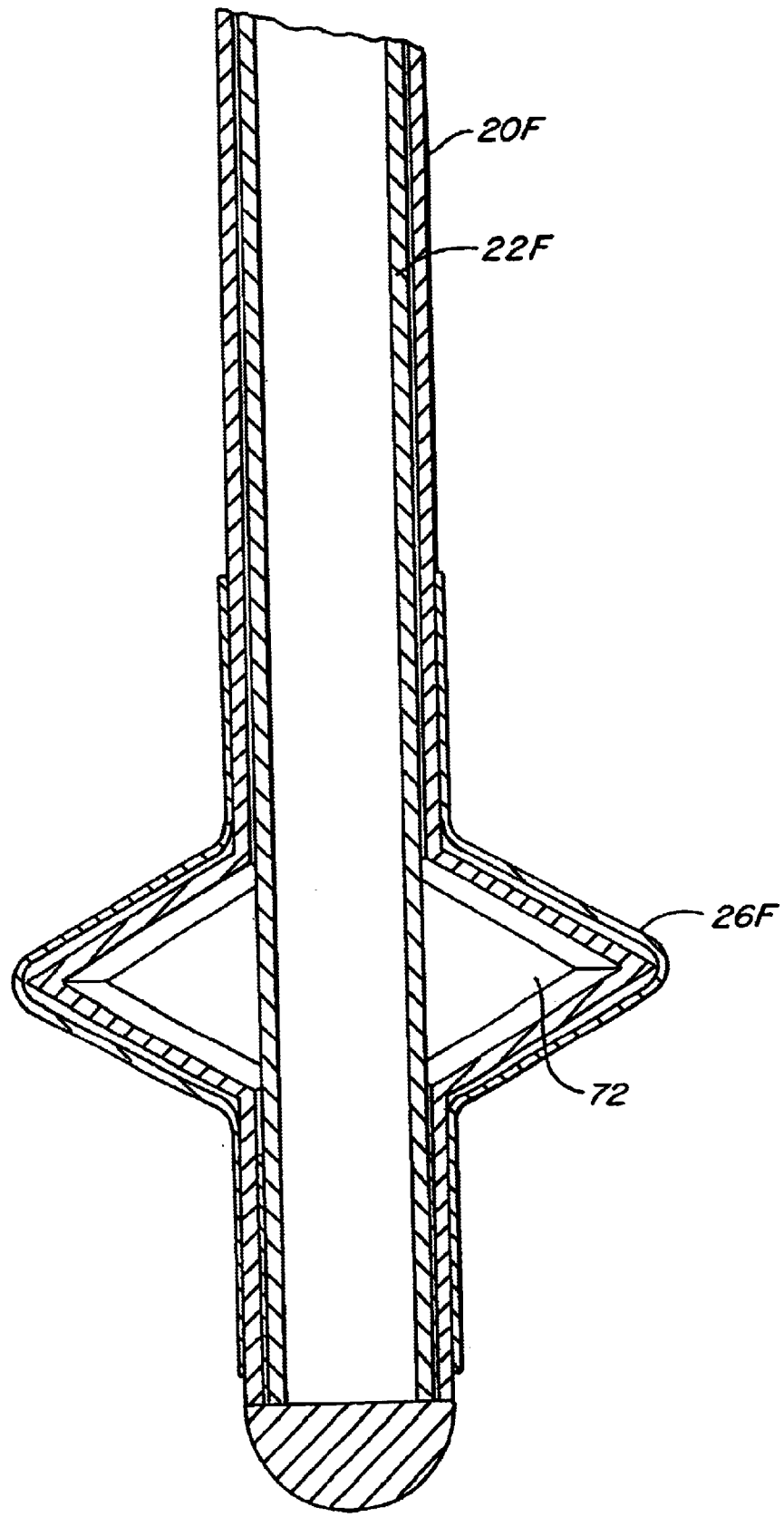

FIG. 13 illustrates a further barrier assembly 4F which uses, as shown in FIGS. 13A and 13B, an outer tube 20F as the barrier carrier and an inner tube 22F as the barrier actuator. Barrier 26F is mounted over the distal end of outer tube 20F. Outer tube 20F has a number, such as four, of axially-extending slits 72 located centrally beneath barrier 26F. Pulling inner tube 22F axially relative to outer tube 20F causes the slit region of the outer tube to buckle outwardly from the collapsed condition of FIG. 13 to the expanded, deployed condition of FIGS. 13A–13E.

Figure 13C:
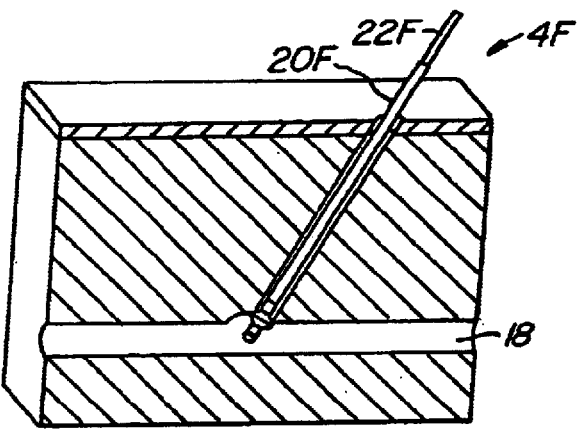
FIG. 13C shows the barrier assembly of FIG. 13 with the barrier in the deployed condition of FIGS. 13A and 13B and the introducer sheath removed.
Figure 13D:
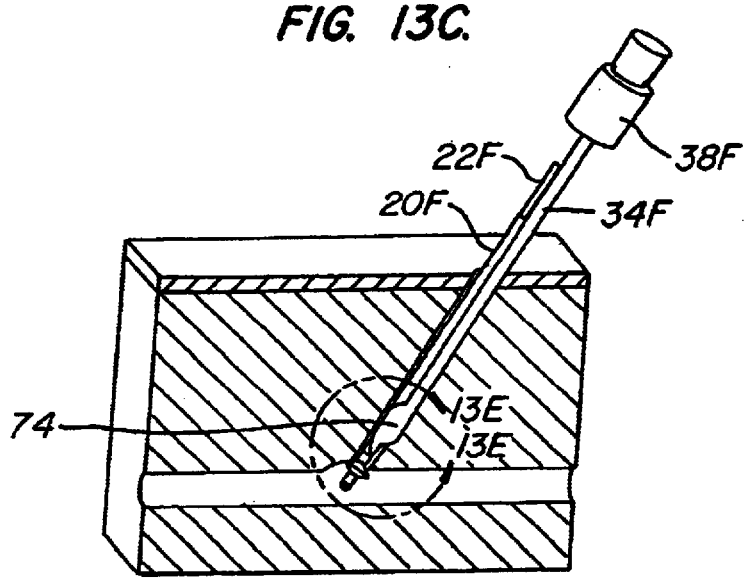
FIG. 13D shows the barrier assembly of FIG. 13C with the distal end of a flowable material delivery tube positioned adjacent the deployed barrier.
Figure 13E:
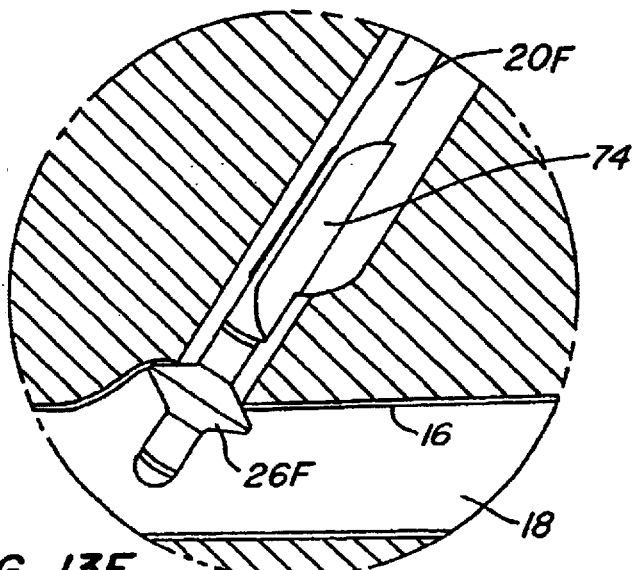
FIG. 13E is an enlarged view of the distal ends of the barrier assembly and delivery tube of FIG. 13D.

FIG. 13 shows barrier assembly 4F having been passed through introducer sheath 10 with barrier 26F within blood vessel 18. FIG. 13C illustrates barrier 26F in a deployed condition, pressed against the wall 16 of the blood vessel with introducer sheath 10 removed. FIG. 13D shows a delivery tube 34F having an integral tube clip 74, see FIG. 13E, at its distal end which clips to and slides along outer tube 20F. Fitting 38F can be coupled a source of hemostatic flowable material, such as a syringe.

Figure 14:
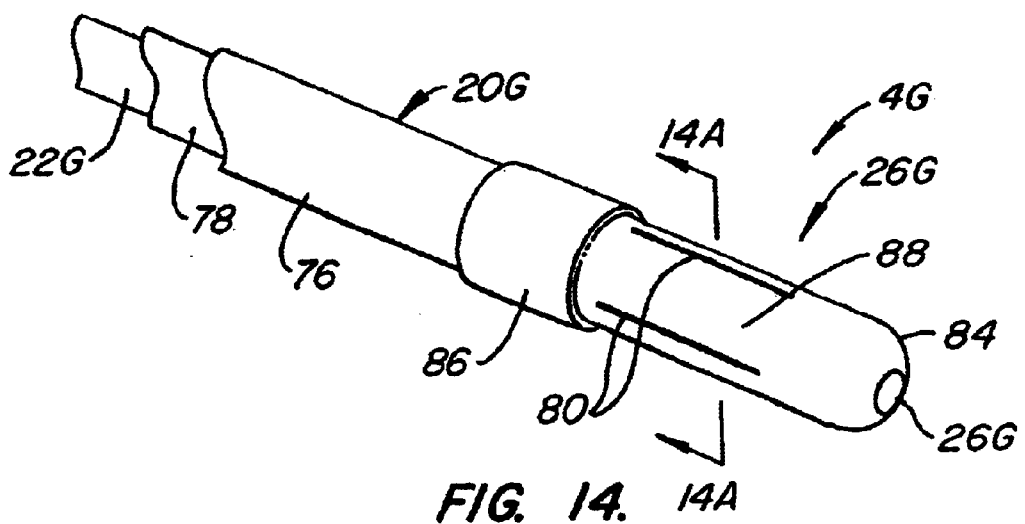
FIG. 14 is an enlarged isometric view of the distal portion of a further barrier assembly made according to the invention with the barrier in a collapsed configuration.
Figure 14A:
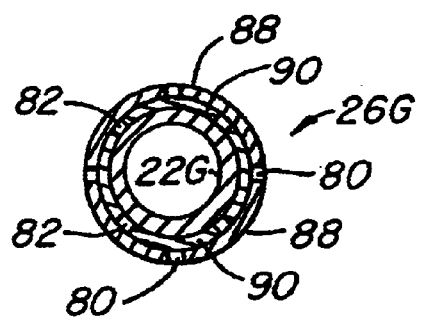
FIG. 14A is a simplified cross-sectional view taken along line 14A—14A of FIG. 14.
Figure 14B:
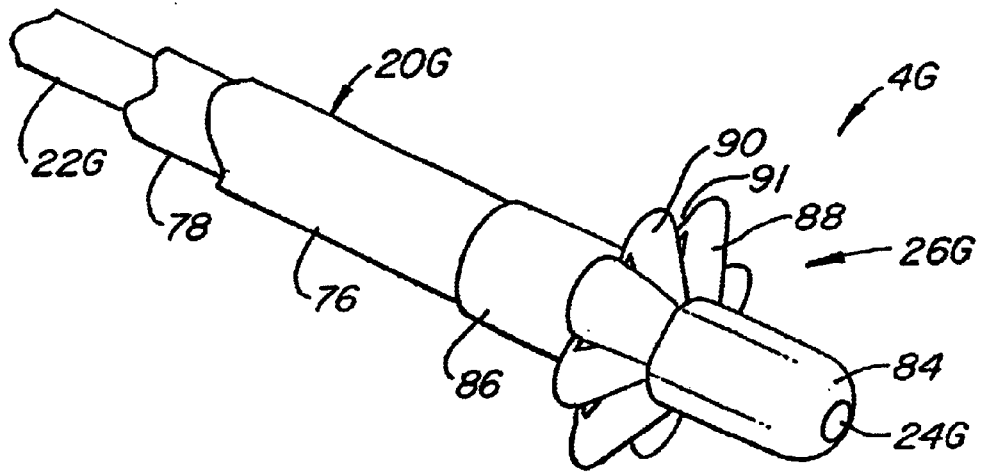
FIG. 14B illustrates the barrier assembly of FIG. 14 with the barrier in a laterally-expanded, fluid-flow-permitting configuration.

FIG. 14 illustrates the distal end of the further alternative embodiment of a barrier assembly 4G which is somewhat similar to the embodiment of FIG. 13B but differs primarily in that it does not include the semipermeable barrier 26F of the FIG. 13B embodiment. Barrier assembly 4 includes a barrier carrier 20G including a first, outer barrier carrier tube 76 and a second, inner barrier carrier tube 78. Tubes 76, 78 each have a series of four equally-spaced slits 80, 82, see FIG. 14A, at their distal ends. Slits 80, 82 are located between the tip 84 of barrier carrier 20G and a metallic stop ring 86, the use of which is described below. Tubes 76, 78 are free to move relative to one another in the area of slits 80, 82. However, tubes 76, 78 are prevented from any significant relative longitudinal or rotational movement so that by pulling on barrier actuator 22G, both tubes 76, 78 buckle in the region of slits 80, 82. This causes the laterally-expandable arms 88, 90 to buckle, that is deflected outwardly, to the deployed configuration of FIG. 14B. As seen in FIGS. 14A and 14B, slits 80, 82 are circumferentially offset so arms 90 of inner barrier carrier tube 78 extend through the opening created between the outwardly deflected arms 88 of outer barrier carrier tube 76. Laterally expanded arms 88, 90 create a number of fluid-flow-permitting gaps 91, see FIG. 4B. Gaps 91 are small enough to prevent flow of hemostatic flowable material 30 therethrough but large enough to permit passage of a suitable amount of blood into tissue track 12 for interaction with material 30.

FIG. 15 illustrates a further embodiment of the invention using barrier assembly 4G of FIG. 14. Barrier assembly 4G is housed within a spacer tube 92, the spacer tube being housed within a hollow delivery tube 34H. The distal end 94 of spacer tube 92 abuts stop ring 86 and is tapered to provide a smooth transition between barrier assembly 4G and delivery tube 34H as tube 92 is introduced into tissue track 12. Once in position within tissue track 12, barrier actuator 22G is pulled thus causing arms 88, 90 to be laterally expanded so that the barrier is in a deployed position. Spacer tube 92 is then partially withdrawn as shown in FIG. 15A to permit material 30 to be introduced into the generally annular flowable material path 96 defined between delivery tube 34H and barrier carrier tube 76. Flowable material 30 passes through a flowable material delivery port 98 at the proximal end of delivery tube 34H, along path 96 and out of the exit 99 of path 96. The embodiment of FIGS. 15 and 15A permits the flowable material to be properly introduced adjacent to barrier 26G and backfilled up into tissue path 12. After tissue track 12 is properly filled with material 30, spacer tube 92 and delivery tube 34H can be removed from barrier carrier 20G. When appropriate, barrier actuator 22G is pushed distally causing barrier 26G to move to the collapsed configuration of FIG. 14 to permit barrier assembly 4G to be removed from the tissue track.

FIGS. 16 and 16A illustrate a further embodiment of the invention incorporating barrier assembly 4G of FIG. 14 together with a laterally collapsible delivery tube 34I. Laterally-collapsible delivery tube 34I is mounted over outer barrier carrier tube 76 and defines a flexible, laterally-collapsible flowable material path 100 having an entrance 102 at a proximal end of path 100 and an exit 104 at a distal end of path 100 adjacent to barrier 26G. Material 30 is introduced into path 100 at entrance 102 through the use of a tube 106 having a fitting 108 at its proximal end coupleable to a conventional syringe or other supply of hemostatic flowable material 30. Tube 106 need not be inserted very far along path 100 of tube 34I to provide a sufficient seal between laterally-collapsible tube 34I and tube 106. In the preferred embodiment tube 34I is made of heat-shrinkable polyester; however, other materials, such as PET, PETG or PVC, could also be used. Path 100 is shown in FIG. 16A as being somewhat kidney-shaped. Other shapes for path 100 when laterally-collapsible tube 34I is in its expanded or extended condition can also be used. In this preferred embodiment, laterally-collapsible tube 34I is mounted over outer barrier carrier tube 76 through the use of an integral mounting sleeve 110 surrounding tube 76. If desired, other methods of mounting tube 34I to tube 76 could be used, such as through the use of an adhesive or heat bonding.

With the embodiment of FIG. 16, barrier assembly 4G with delivery tube 34I mounted thereto is typically deployed through an introducer sheath. The introducer sheath would then be removed, actuator 22G would be actuated to cause barrier 26G to be deployed, and material 30 would be introduced into percutaneous tissue track 12 using tube 106 inserted through entrance 102 of flowable material path 100. When it is time to remove barrier assembly 4G, barrier actuator 22G is pushed distally relative to tubes 76, 78 causing barrier 26 to move from the deployed configuration shown in FIG. 14B to the undeployed configuration of FIG. 14. Barrier assembly 4G and flowable material delivery tube 34I therewith can then be removed from tissue track 12.

Other modifications and variations can be made to the enclosed embodiments without departing from the subject of the invention as defined in the following claims.

Any and all patents, applications and printed publications referred to above are incorporated by reference.

What is claimed is:

1. A percutaneous tissue track closure assembly comprising:
   a barrier assembly comprising:
   an elongate barrier carrier having a distal end;
   a semipermeable barrier which permits blood or at least one blood component to pass therethrough but prevents the flowable material from passing therethrough and which comprises a plurality of laterally-expandable arms defining fluid-flow-permitting gaps therebetween when in the deployed configuration at the distal end of the barrier carrier, the barrier being placeable in a laterally retracted, undeployed configuration and a laterally expanded, deployed configuration; and
   a user-operated barrier actuator coupled to the barrier to move the barrier between the undeployed and deployed conditions;
   a flowable material assembly comprising:
   a source of a hemostatic flowable material;
   a delivery tube having a tube entrance and a tube exit at a chosen position along the barrier carrier, the delivery tube coupleable to the flowable material source; and
   a flowable material driver selectively driving flowable material from the flowable material source through the tube entrance, along the delivery tube and out of the delivery tube through the tube exit.

2. The assembly according to claim 1 wherein said semipermeable barrier comprises a porous mesh material.

3. The assembly according to claim 1 wherein said semipermeable barrier comprises a semipermeable membrane.

4. The assembly according to claim 1 wherein said barrier carrier comprises a barrier carrier tube having longitudinally-extending weakened regions defining laterally-expandable arms, said arms defining fluid-flow-permitting gaps therebetween when in the deployed configuration.

5. The assembly according to claim 4 comprising first and second of said barrier carrier tubes, said first and second barrier carrier tubes being generally coaxial with the second tube being housed within the first tube, the longitudinally-extending weakened regions of said first tube being circumferentially offset from the weakened regions of the second tube.

6. The assembly according to claim 4 wherein said weakened regions are slits in the barrier carrier tube.

7. The assembly according to claim 1 wherein the flowable material is bioabsorbable.

8. The assembly according to claim 1 wherein the hemostatic flowable material swells upon contact with blood.

9. The assembly according to claim 1 wherein the hemostatic flowable material comprises at least one of a blood clotting agent and a material which swells upon contact with an aqueous fluid.

10. The assembly according to claim 1 wherein said source of flowable material comprises a granulated gel material which swells on contact with blood.

11. The assembly according to claim 10 wherein the barrier is a semipermeable barrier which permits passage of blood therethrough but prevents passage of the granulated gel material therethrough.

12. The assembly according to claim 1 wherein said source of flowable material comprises a syringe containing a granulated gel material and thrombin.

13. The assembly according to claim 1 wherein said delivery tube has open proximal and distal ends which constitute the tube entrance and exit, respectively.

14. The assembly according to claim 1 wherein the elongate barrier carrier is mounted within the delivery tube to define a flowable material path therebetween.

15. The assembly according to claim 14 wherein the flowable material path is a generally annular path.

16. The assembly according to claim 1 wherein the delivery tube comprises a laterally collapsible tube.

17. The assembly according to claim 16 wherein the collapsible tube is mounted to and external of the elongate barrier carrier.

18. The assembly according to claim 16 wherein the collapsible tube is made of heat-shrinkable polyester.

19. The assembly according to claim 1 wherein the barrier carrier comprises a tubular barrier carrier.

20. The assembly according to claim 19 wherein the barrier actuator is housed within and moves longitudinally within the barrier carrier to move the barrier between the undeployed and deployed conditions.

21. The assembly according to claim 1 wherein the barrier actuator is positioned generally parallel to and external of the barrier carrier.

22. The assembly according to claim 1 further comprising a delivery tube alignment device for aligning the tube exit at said chosen position.

23. The assembly according to claim 22 wherein the delivery tube alignment device comprises a thread secured to and extending from the distal end of the barrier, the thread passing through the delivery tube.

24. The assembly according to claim 22 wherein the delivery tube alignment device comprises a first visual indicator on the delivery tube.

25. The assembly according to claim 24 wherein the delivery tube alignment device comprises a second visual indicator, for positioning relative to the first visual indicator, on the barrier carrier.

26. The assembly according to claim 22 wherein the delivery tube alignment device comprises a guide secured to and extending laterally from a chosen one of the barrier carrier and the delivery tube, said guide slidable along the other of the barrier carrier and the delivery tube.

27. The assembly according to claim 22 wherein the delivery tube alignment device further comprises a stop element preventing movement of the delivery tube exit past said chosen position.

28. The assembly according to claim 22 wherein the delivery tube alignment device comprises mating sliding elements on the barrier carrier and the delivery tube.

29. The assembly according to claim 1 wherein the chosen position along the barrier carrier is adjacent to the distal end of the barrier carrier.

30. The assembly according to claim 28 wherein the mating sliding elements comprise a slide member, having an enlarged outer end, extending from a chosen one of the barrier carrier and the delivery tube, and an opening formed in the other of the barrier carrier and the delivery tube sized to accept the enlarged outer end of the slide member.

31. The assembly according to claim 1 wherein:
the delivery tube comprises a distal end; and
the tube exit comprises a first tube exit opening adjacent to the distal end of the delivery tube and second tube exit opening at a position spaced-apart from the first tube exit opening.

32. The assembly according to claim 1 wherein a unitary structure constitutes the barrier carrier, the delivery tube and the delivery tube alignment device.

33. A method for closing a percutaneous tissue track leading to an access opening in a blood vessel comprising the following steps:
selecting a barrier assembly comprising a barrier carrier and a semipermeable barrier at the distal end of the barrier carrier, the barrier configured to permit at least one blood component to pass therethrough when in a laterally expanded, deployed configuration;
inserting the barrier through a tissue track and through an access opening in a blood vessel, the barrier being in a laterally retracted, undeployed configuration while housed within a delivery tube, the barrier carrier and the delivery tube defining a flowable material path therebetween;
placing the barrier in the laterally expanded, deployed configuration against the access opening;
filling at least a portion of the tissue track adjacent to the access opening with a hemostatic flowable material, said flowable material being of a type which does not pass through the barrier;
maintaining the barrier in position for a chosen time period thereby preventing the flowable material from passing through the barrier into the blood vessel while permitting the at least one blood component to flow through the barrier to interact with the hemostatic flowable material to seal effectively the tissue track;
placing the barrier in the laterally retracted, undeployed condition after said chosen period of time;
removing a spacer tube from the flowable material path prior to the filing step; and
removing the barrier from the blood vessel and the tissue track so the flowable material effectively seals the percutaneous tissue track.

34. The method according to claim 33 wherein said filling step takes place with the hemostatic flowable material being chosen to do at least one of the following:
swell on contact with the at least one blood component; and
cause the at least one blood component to clot.

35. The method according to claim 33 wherein the inserting step is carried out through an introducer catheter extending along the tissue track.

36. The method according to claim 35 further comprising the step of removing the introducer catheter from the tissue track after the inserting step.

37. The method according to claim 33 wherein the filling step comprises flowing the flowable material through a laterally collapsible tube mounted to the barrier carrier.

38. The method according to claim 33 wherein the filling step comprises the step of selecting a granulated material as the bioabsorbable flowable material.

39. The method according to claim 38 wherein the selecting step is carried out with the granulated material being a granulated gel material.

40. The method according to claim 33 wherein the filling step comprises the step of selecting a bioabsorbable, flowable material including thrombin.

41. The method according to claim 33 wherein the barrier placing step comprises the step of pulling on the barrier.

42. The method according to claim 33 wherein said barrier placing step is carried out with the barrier carrier comprising a first barrier carrier tube and wherein the barrier is defined at least in part by a plurality of laterally-expandable first arms created by longitudinally-extending first weakened regions in the first barrier carrier tube.

43. The method according to claim 42 wherein the barrier placing step comprises axially compressing the first barrier carrier tube so to cause the laterally-expandable first arms to be deflected outwardly with fluid-flow-permitting gaps defined therebetween.

44. The method according to claim 43 wherein the barrier carrier placing step is carried out with the barrier carrier comprising a second barrier carrier tube housed within the first barrier carrier tube, the barrier being defined at least in part by the outwardly deflected first arms and a plurality of outwardly deflected second arms created by longitudinally-extending second weakened regions in the second barrier carrier tube.

45. The method according to claim 33 wherein the filling step comprises the steps of:
   positioning an open exit end of a delivery tube at or near the access opening; and
   forcing the flowable material through the open exit end.

46. The method according to claim 45 wherein the positioning step comprises the steps of:
   passing a filament, secured to the distal end of the barrier carrier at a chosen position, completely through the delivery tube; and
   positioning the delivery tube exit end at the chosen position.

47. The method according to claim 46 wherein the filling step comprises the step of moving the exit end of the delivery tube in a proximal direction away from the barrier thereby back-filling the tissue track with the flowable material.

48. The assembly according to claim 47 wherein said semipermeable barrier comprises at least two laterally-extendable arms defining fluid-flow-permitting gaps therebetween when in the deployed configuration.

49. The assembly according to claim 48 wherein the arms are nonporous.

50. A method for sealing a percutaneous tissue track extending to a blood vessel comprising:
   establishing a semipermeable barrier at a distal end of the tissue track adjacent to a blood vessel access opening, the semipermeable barrier permitting passage of at least one blood component therethrough and preventing passage of a chosen hemostatic material therethrough, said establishing step being carried out using a plurality of laterally expansible arms defining fluid flow, permitting gaps therebetween when laterally expanded; and
   introducing the chosen hemostatic material into the tissue track, wherein the at least one blood component passing through the semipermeable barrier interacts with the chosen hemostatic material to seal effectively the tissue track while the semipermeable barrier prevents passage of the hemostatic material into the blood vessel lumen.

51. The method according to claim 50 wherein the blood-permeable barrier establishing step is carried out by deploying the blood-permeable barrier adjacent to an internal surface of the lumen of the blood vessel.

52. The method according to claim 33 wherein the establishing step comprises the step of expanding the blood-permeable barrier from a laterally-collapsed condition to a laterally-extended condition.

53. The method according to claim 50 wherein the establishing step comprises:
   advancing the blood-permeable barrier distally through the tissue track in a collapsed condition; and
   deploying the blood-permeable barrier within the lumen of the blood vessel and against a wall of the blood vessel.

54. The method according to claim 53 further comprising the steps of:
   collapsing the blood-permeable barrier after the tissue track has been effectively sealed; and
   removing the collapsed blood-permeable barrier.

55. The method according to claim 50 wherein the introducing step comprises injecting the chosen hemostatic material through a cannula.

56. The method according to claim 55 wherein the injecting step is carried out using a cannula having a size of 15 gauge or smaller.

57. The method according to claim 50 wherein the introducing step is carried out with a flowable gel hemostatic material.

58. The method according to claim 50 wherein the introducing step is carried out with a flowable gel hemostatic material comprising a matrix material and at least one clotting agent which interacts with the at least one blood component to enhance clotting.

59. The method according to claim 58 wherein the introducing step is carried out with the matrix material comprising at least one protein.

60. The method according to claim 58 wherein the introducing step is carried out with the clotting agent comprising at least one of the following proteins: thrombin, fibrin, and fibrinogen.

61. The method according to claim 50 wherein the introducing step is carried out with the chosen hemostatic material comprising a first material which swells upon contact with the at least one blood component and a second material which induces clotting of the at least one blood component.

62. The method according to claim 50 wherein the introducing step comprises flowing the hemostatic material along a path defined between a barrier carrier tube, to which the semipermeable barrier is mounted, and an elongate inner member, mounted within the barrier carrier tube.

63. The method according to claim 50 wherein the introducing step comprises flowing the hemostatic material through a laterally collapsible tube.

64. The method according to claim 50 wherein the establishing step is carried out using a semipermeable membrane which permits blood to flow therethrough.

* * * * *